United States Patent [19]

Kawashima et al.

[11] 4,305,935

[45] Dec. 15, 1981

[54] BONE FORMATION STIMULANT

[75] Inventors: Hiroyuki Kawashima, Van Nuys, Calif.; Minoru Hayashi, Hachioji, Japan; Seiji Kurozumi; Yoshiki Suzuki, both of Hino, Japan; Yoshinobu Hashimoto, Fujisawa, Japan

[73] Assignee: Teijin Limited, Osaka, Japan

[21] Appl. No.: 196,223

[22] PCT Filed: Mar. 12, 1979

[86] PCT No.: PCT/JP79/00063

§ 371 Date: Apr. 9, 1980

§ 102(e) Date: Apr. 3, 1980

[87] PCT Pub. No.: WO80/00304

PCT Pub. Date: Mar. 6, 1980

[30] Foreign Application Priority Data

Aug. 9, 1978 [JP] Japan .................................. 53-96079

[51] Int. Cl.$^3$ ........................................... A61K 31/605

[52] U.S. Cl. .................................... 424/235; 424/236; 424/343

[58] Field of Search ......................................... 424/235

[56] References Cited

PUBLICATIONS

Hiroyuki et al.–Study of Biol. Activity Vit. D Effect on Aspirin (Teijin Inst. for Bio-Med. Res.) 10th report, Mar. 14, 1978.
Boris et al.–Chem. Abst., vol. 88 (1978), p. 169d.
Reynolds et al.–Chem. Abst., vol. 82 (1975), p. 68069c.
Jett et al.–Chem. Abst., vol. 77 (1972), p. 83820f.

Primary Examiner—Sam Rosen
Attorney, Agent, or Firm—Sughrue, Mion, Zinn, Macpeak and Seas

[57] ABSTRACT

This is a bone formation stimulant containing vitamin $D_3$ or its derivative and acetylsalicylic acid or its formaceutically permissible salt. The present bone formation stimulant is used to cure or prevent the diseases caused by the deficiency of vitamin D or related diseases by dosing human beings or animals with it.

4 Claims, No Drawings

BONE FORMATION STIMULANT

TECHNICAL FIELD

The present invention relates to a bone formation stimulant consisting of vitamin $D_3$ or its derivative and acetylsalicylic acid or its pharmaceutically permissible salt.

BACKGROUND ART

It is known that vitamin $D_3$ or its derivative is related with the calcium metabolism, or intestinal calcium absorption, dissolution of bone salts in the bone tissues and bone formation of warm-blooded animals and is expected to be used as a remedy or a preventive for diseases resulting from anormal calcium metabolism such as renal ostes dystrophy, parathyroid insufficiency, osteoporosis, osteomalacia, syndrom of absorption disturbances, etc. However, vitamin $D_3$ or its derivative presents a problem that its excess dosage causes a seriously harmful subsidiary effects since it also has a function of dissolving the bone salts. Expectations may therefore be held that vitamin $D_3$ or its derivative can be used as a bone formation stimulant with greater safety, if only the function of dissolving the bone salts can be depressed among the functions of vitamin $D_3$ or its derivative while such functions as the promotion of the absorption of calcium from the intestinal tract and the stimulation of ossifying function in the bone tissue are well preserved.

The present inventors, having conducted a research on the bone salt dissolving function of $1\alpha$-hydroxycholecalciferol, one of the derivatives of vitamin $D_3$, came to know and already made it public (at the general meeting held by the Japanese Pharmacological Society on Mar. 25, 1978, at Sendai) a fact that, after a series of tests with the use of rats, which have undergone thyreoidectomy and parathyroidectomy and have been kept in the state of hypocalcemia, the bone salt dissolving function (which is noticed by the rise in the ionic concentration of the serum calcium) can be depressed by dosing acetylsalicylic acid. However, in said publication, it was not made clear how acetylsalicylic acid influenced the ossifying function of $1\alpha$-hydroxycholecalciferol. Because it has been known that in the bone tissues of the warm-blooded animals the bone salt dissolution and the ossification are carried out side by side simultaneously and it has been regarded that which of these mutually contradictory functions holds greater prominence is a matter of complication depending not only on the functions of the vitamin $D_3$ derivative but also on the serum calcium ion, phosphorus, thyroid hormone, parathormone, calcitonin, corticosteroid, plostaglandin, etc.

The present inventors, based on the knowledge of said function peculiar to acetylsalicylic acid, continued the persistent efforts to develop the research and came to find that acetylsalicylic acid (or its pharmaceutically permissible salt) does not interfere with vitamin $D_3$ or its derivative in its functions of absorbing calcium from the intestinal tract and of ossifying in the bone tissues and it favorably stimulates the ossifying function of vitamin $D_3$ or its derivative not only in the warm-blooded animals subjected to hypocalcemia but also in the warm-blooded animal in normal condition.

DISCLOSURE OF INVENTION

Based on the said knowledge, the present inventors further carried on the research with the purpose of offering a bone formation stimulant which is convenient to use and free from harmful side effects and came to complete this invention.

More specifically, the present invention is related to a bone formation stimulant consisting of vitamin $D_3$ or its derivative and acetylsalicylic acid or its pharmaceutically permissible salt.

According to the present invention, the function of vitamin $D_3$ or its derivative to dissolve bone salts and related harmful side effects are checked and the ossifying function of vitamin $D_3$ or its derivative is displayed with superiority in function to the former. Such a functional effect can be achieved by dosing the warm-blooded animals with vitamin $D_3$ or its derivative and acetylsalicylic acid or its pharmaceutically permissible salt separately; however, in this case, inconvenience is experienced with the necessity of a strict dose control base on a prescription prepared by a physician or a pharmacist. On the contrary, it is characterized in the present invention that when vitamin $D_3$ or its derivative and acetylsalicylic acid or its pharamceutically permissible salt is made into a compound medicine according to the present invention, only the merits of vitamin $D_3$ or its derivative are set forth and the harmful side effects are depressed.

BEST MODE OF CARRYING OUT THE INVENTION

In the present invention, vitamin $D_3$ or its derivative is expressed by the following formula [I]:

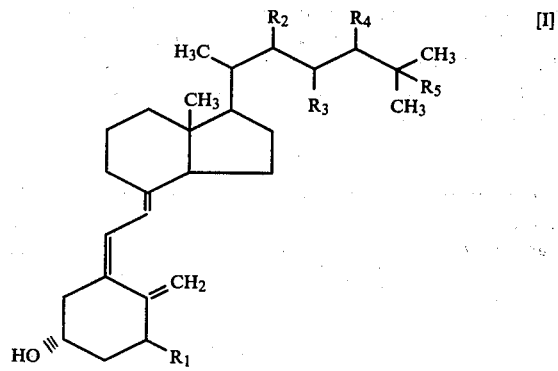

where $R_1$, $R_2$, $R_3$, $R_4$ and $R_5$ are the same or different and are hydrogen atoms or hydroxyl groups.

Derivatives of vitamin $D_3$ may be embodied, for instance, by $1\alpha$-hydroxycholecalciferol, $1\alpha,25$-dihydroxycholecalciferol, $1\alpha,24$-dihydroxycholecalciferol, $1\alpha,24(S)$-dihydroxycholecalciferol, $1\alpha,24(R)$-dihydroxycholecalciferol, $1\alpha,24,26$-trihydroxycholecaliferol, $1\alpha,22$-dihydroxycholecalciferol, $24,25$-dihydroxycholecalciferol, etc.

In the present invention, $1\alpha$-hydroxycholecalciferol, $1\alpha,24(R)$-dihydroxycholecalciferol, $1\alpha,25$-dihydroxycholecalciferol, and $24,25$-dihydroxycholecalciferol are especially preferable.

These compounds can be prepared from steroids such as cholesterol, etc. according to publicly known methods (for instance, these methods disclosed in Japanese Patent Application Laid-Open Nos. 62750/73, 26316/78, etc.).

As for the pharmaceutically permissible salts of acetylsalicylic acid in the present invention, for example, aluminum acetylsalicylate, choline acetylsalicylate, lysine acetylsalicylate, etc. may be mentioned.

The bone formation stimulant simultaneously containing the said two ingredients in the present invention may take the form of a pressed tablet, coated tablet, rigid or soft gelantinous capsule, oil or aqueous solution or emulsion for oral dosage. As for the solvents for oil solutions, vegetable oils such as coconut oil, corn oil, cotton seed oil, and peanut oil, or liver oil, or oily ester such as polysorbate 80 may be used. In case when rectal dose is required, it may take the form of a suppository with cacao butter or other triglycerides used as a base.

It may be prepared in the form of an ethyl alcohol solution for animal injection use.

The preferable dosage of vitamin $D_3$ or its derivative is 0.1–10 $\mu$g/day/person and that of acetylsalicylic acid or its pharmaceutically permissible salt is 0.1–10 g/day/person. Therefore, the bone formation stimulant of the present invention consisting of vitamin $D_3$ or its derivative and acetylsalicylic acid or its pharmaceutically permissible salt is prepared in such a way as to maintain the abovementioned quantitative relationship, to be taken in 1 to 3 doses per day. It is preferable to have the ratio between the two ingredients of the bone formation stimulant according to the present invention kept in the range of 0.01 to $100 \times 10^{-6}$ part by weight of vitamin $D_3$ or its derivative per 1 part by weight of acetylsalicylic acid or its pharmaceutically permissible salt.

It is advantageous to mix an antioxidant such as ascorbic acid, butyl hydroxy-anisole, and hydroquinone with the bone formation stimulant of the present invention to lengthen its storage life. The present preparation can take the form of an inclusion compound by use of $\beta$-cyclic dextrin for the purpose of stabilization.

The following examples are illustrative of the present invention in detail.

EXAMPLE 1

This example shows that the increase of the serum calcium level due to the dissolution of bone salts of the warm-blooded animals caused by a derivative of vitamin $D_3$ is checked by the administration of acetylsalicylic acid.

Experiment (1)

The rats were subjected to thyroidectomy and parathyroidectomy under ether anesthesia (with the purpose of eliminating the dissolution of bone salts due to parathyroid hormone and calcitonin) and the rats were left unfed overnight. Those whose serum calcium level was 6 mg/dl or below were used in the following experiment. Twenty-four hours after the extirpation was carried on, the rats were given an injection of 2.5 $\mu$g/kg of $1\alpha$-hydroxycholecalciferol ($1\alpha$-OH-$D_3$) and the serum calcium level was measured 20 hours later. Acetylsalicylic acid was given orally 30 minutes before the administration of $1\alpha$-OH-$D_3$.

During the experiment, the rats were given feed of low calcium so that the absorption of calcium from the intestinal tract might be negligible and the increase of the serum calcium level would actually correspond to the degree of dissolution of bone salts.

The results are shown in Table 1.

TABLE 1

| | Administered medicine | | |
|---|---|---|---|
| No. | $1\alpha$-OH—$D_3$ ($\mu$g/Kg, i.p.) | Acetylsalicylic acid (mg/Kg, p.o.) | Serum calcium $\Delta$Ca (mg/dl)*2 Average ± standard error |
| 1 | 2.5 | 0 | 1.45 ± 0.23 (7)*1 |
| 2 | 2.5 | 200 | −12.1 ± 0.42 (6) |

Notes:
*1: The numerical value in parentheses indicates the number of the rats. (The same shall apply in the following tables.)
*2: $\Delta$Ca indicates the difference from the control value by the formular of "average ± standard error". (The same shall apply in Tables 2 to 4).

As shown in Table 1 above, in case where $1\alpha$-OH-$D_3$ was administered solely, it is clear that the serum calcium level rose to indicate that the dissolution of bone salts took place. On the other hand, when acetylsalicylic acid was administered together with $1\alpha$-OH-$D_3$, no significant increase of the serum calcium level was noticed which shows that the action of $1\alpha$-OH-$D_3$ to dissolve the bone salts was restrained.

Experiment (2)

Rats were prepared according to Experiment (1) after they were subjected to parathyroidectomy (with the purpose of eliminating the dissolution of bone salts due to parathyroid hormone) and the experiment was conducted in accordance with the same procedure as in Experiment 1.

The results are shown in Table 2.

TABLE 2

| | Administered medicine | | |
|---|---|---|---|
| No. | $1\alpha$-OH—$D_3$ ($\mu$g/Kg, i.p.) | Acetylsalicylic acid (mg/Kg, p.o.) | Serum calcium $\Delta$Ca (mg/dl) Average ± standard error |
| 1 | 2.5 | 0 | 1.88 ± 0.29 (5) |
| 2 | 0 | 200 | −0.47 ± 0.33 (6) |
| 3 | 2.5 | 200 | −0.55 ± 0.36 (5) |

It is clear from Table 2 that, when $1\alpha$-OH-$D_3$ was administered solely, the serum calcium level rose to indicate that the dissolution of bone salts took place. On the other hand, when acetylsalicylic acid was dosed in combination with $1\alpha$-OH-$D_3$, no significant increase of the serum calcium level was noticed which shows that the action of $1\alpha$-OH-$D_3$ to dissolve the bone salts was restrained.

Experiment (3)

The rats were subjected to thyroidectomy and parathyroidectomy under ether anethesia, followed immediately by nephrectomy in which both kidneys were removed (with the purpose of checking the dissolution of bone salts due to parathyroid hormone and the function of kidneys to discharge calcium as well) and the rats were left unfed overnight. Those rats whose serum calcium level was 6 mg/dl or below were used in the following experiment.

The experiment was conducted in accordance with Experiment (1), excepting that the serum calcium level was measured 8 hours after the administration of $1\alpha$-OH-$D_3$.

The results are shown in Table 3.

TABLE 3

| No. | Administered medicine 1α-OH—D$_3$ (μg/Kg, i.p.) | Acetylsalicylic acid (mg/Kg, p.o.) | Serum calcium ΔCa (mg/dl) Average ± standard error |
|---|---|---|---|
| 1 | 2.5 | 0 | 0.39 ± 0.29 (7) |
| 2 | 2.5 | 20 | −0.48 ± 0.14 (5) |
| 3 | 2.5 | 50 | −0.79 ± 0.43 (4) |

It is clear from Table 3 that, when 1α-OH-D$_3$ was administered alone, the serum calcium level rose; however, when 1α-OH-D$_3$ was dosed together with acetylsalicylic acid, no significant increase of the serum calcium level was noticed.

Experiment (4)

The experiment was conducted according to Experiment (1), wherein 1α,24-dihydroxycholecaliferol (1α,24-(OH)$_2$-D$_3$) was dosed in the place of 1α-OH-D$_3$ used in Experiment (1). The results are shown in Table 4.

TABLE 4

| No. | Administered medicine 1α,24-(OH)$_2$—D$_3$ (μg/Kg, i.p.) | Acetylsalicylic acid (mg/Kg, p.o.) | Serum calcium ΔCa (mg/dl) Average ± standard error |
|---|---|---|---|
| 1 | 2.5 | 0 | 2.33 ± 0.71 (5) |
| 2 | 0 | 200 | 0.22 ± 0.30 (4) |
| 3 | 2.5 | 200 | 0.71 ± 0.53 (5) |

It is clear from Table 4 that, when 1α,24-(OH)$_2$-D$_3$ was administered alone, the serum calcium level rose remarkably; however, when 1α,24-(OH)$_2$-D$_3$ was dosed together with acetylsalicylic acid, the increase of the serum calcium level was very small. Experiment (5)

This experiment was conducted with the purpose of showing the variation of the serum calcium level (absolute value) obtained with the normal rats subjected to the continued administration of 1α,25-dihydroxycholecalciferol (1α,25-(OH)$_2$-D$_3$) and acetylsalicylic acid.

1α,25-(OH)$_2$-D$_3$ was administered orally to the normal rats at the rate of 0.25 μg/Kg/day for 15 days and the serum calcium level was measured 24 hours after the last dose was given to the rats. Acetylsalicylic acid was also administered orally along with 1α,25-(OH)$_2$-D$_3$ at the rate of 10 mg/Kg/day for 15 days.

During the period of experiment, the rats were given normal feed equal in weight ot their body weight.
The results are shown in Table 5.

TABLE 5

| No. | Administered medicine 1α,25-(OH)$_2$—D$_3$ (μg/Kg/day p.o. 15 days) | Acetylsalicylic acid (mg/Kg/day p.o. 15 days) | Serum calcium Ca (mg/dl)*1 Average ± standard error |
|---|---|---|---|
| 1 | 0 | 0 | 10.11 ± 0.10 (6) |
| 2 | 0 | 10 | 10.31 ± 0.09 (6) |
| 3 | 0.25 | 0 | 11.18 ± 0.12 (6) |
| 4 | 0.25 | 10 | 10.28 ± 0.19 (6) |

Note:
*1: Ca indicates an absolute value.

It is clear from Table 5 that acetylsalicylic acid has a function to check the increase of the serum calcium level due to 1α,25-(OH)$_2$-D$_3$ in the case where the normal rats are used. Since the normal rats used in this experiment were given normal feed, the rise of the serum calcium level (No. 3 in Table 5) caused by the administration of 1α,25-(OH)$_2$-D$_3$ may be deemed to be encouraged not only by the function of 1α,25-(OH)$_2$-D$_3$ to dissolve bone salts but also by the function of 1α,25-(OH)$_2$-D$_3$ to promote the absorption of calcium from the intestinal tract. When 1α,25-(OH)$_2$-D$_3$ was dosed together with acetylsalicylic acid, the rise of the serum calcium level was checked (No.4). This fact shows that the function of 1α,25-(OH)$_2$-D$_3$ to dissolve the bone salts is checked and the contribution of serum calcium to the osteosis ossification is promoted since actylsalicylic acid has nothing to do with the absorption of calcium from the intestinal tract as shown in Example 2 that follows hereinafter.

Example 2

This example is to show that the function of vitamin D$_3$ derivatives to absorb calcium from the intestinal tract is not influenced by the administration of acetylsalicylic acid.

Experiment (1)

The rats which has been fed on vitamin D deficient feed (so-called vitmin D deficient rats) were subjected to thyroidectomy and parathyroidectomy under ether anesthesia and were left unfed overnight.

24 hours after the operation was carried out, the rats were given an injection of 0.25 μg/Kg of 1α-OH-D$_3$ and the absorption of calcium from the intestinal tract was measured by the everted sac technique 20 hours after the administration of 1α-OH-D$_3$. The serum calcium level was also measured at the same time. The administration of acetylsalicylic acid was effected orally 30 minutes before 1α-OH-D$_3$ was given.

Incidentally, during the whole period while the experiment was carried on the rats were fed on vitamin D deficient feed of low calcium content. The results are shown in Table 6.

TABLE 6

| No. | Administered medicine 1α-OH—D$_3$ (μg/Kg, i.p.) | Acetylsalicylic acid (mg/Kg, p.o.) | Absorption of calcium from intestinal tract ($^{45}$Ca(S)/$^{45}$Ca(M) Average ± standard error | Serum calcium Ca (mg/dl)*1 Average ± standard error |
|---|---|---|---|---|
| 1 | 0 | 0 | 2.20 ± 0.31 (5) | 4.48 ± 0.09 (5) |
| 2 | 0.25 | 0 | 4.59 ± 0.25 (5) | 5.74 ± 0.17 (5) |
| 3 | 0 | 200 | 2.19 ± 0.27 (5) | 4.14 ± 0.04 (5) |
| 4 | 0.25 | 200 | 4.60 ± 0.19 (5) | 4.09 ± 0.07 (5) |

Note:
*1: Ca indicates an absolute value.

Experiment (2)

The vitamin D deficient rats were dosed orally with 200 mg/Kg. of acetylsalicylic acid and 30 minutes later they were given an injection of 2.5 µg/Kg of 1α-OH-$D_3$. 12 hours after such administration, the absorption of calcium from the intestinal tract was measured by the everted sac technique. The results are shown in Table 7.

TABLE 7

| No. | Administered medicine | | Absorption of calcium from intestinal tract ($^{45}$Ca(S)/$^{45}$Ca(M) Average ± standard error |
|---|---|---|---|
| | 1α-OH—$D_3$ (µg/Kg, i.p.) | Acetylsalicylic acid (mg/Kg, p.o.) | |
| 1 | 0 | 0 | 1.98 ± 0.23 (5) |
| 2 | 2.5 | 0 | 3.91 ± 0.46 (5) |
| 3 | 0 | 200 | 1.95 ± 0.20 (5) |
| 4 | 2.5 | 200 | 3.86 ± 0.23 (5) |

It is clear from Table 6 and Table 7 that 1α-OH-$D_3$ stimulates the absorption of calcium from the intestinal tract and that acetylsalicylic acid has no influence on the absorption of calcium from the intestinal tract regardless of the presence of 1α-OH-$D_3$.

EXAMPLE 3

This example shows an influence of a derivative of vitamin $D_3$ and acetylsalicylic acid on the bone formation. The vitamin D deficient rats were given orally a dose of 0.25 or 2.5 µg/Kg/day of 1α,25-$(OH)_2$-$D_3$ for 15 days. Upon completion of such administration, the rats were depleted to death and the thigh-bones were extracted to measure their dry weight, bone salt weight and bone calcium quantity. A dose of 10 mg/Kg/day acetylsalicylic acid was administered orally at the same time with 1α,25-$(OH)_2$-$D_3$ for 15 days.

Incidentally, the rats were fed on vitamin D deficient feed containing 0.45% calcium.

The results are shown in Table 8.

TABLE 8

| No. | Administered medicine | | Dry weight mg Average ± standard error | Bone salt weight mg Average ± standard error | Bone calcium quantity mg Average ± standard error |
|---|---|---|---|---|---|
| | 1α,25-$(OH)_2$—$D_3$ (µg/Kg/day p.o. 15 days) | Acetylsalicylic acid (mg/Kg/day p.o. 15 days) | | | |
| 1 | 0 | 0 | 173.3 ± 3.9 | 65.0 ± 2.9 | 23.1 ± 1.5 |
| 2 | 0 | 10 | 168.9 ± 4.7 | 65.7 ± 3.4 | 23.9 ± 1.2 |
| 3 | 0.25 | 0 | 213.4 ± 6.9 | 106.6 ± 5.8 | 34.3 ± 1.8 |
| 4 | 0.25 | 10 | 197.9 ± 4.8 | 102.4 ± 5.4 | 34.3 ± 2.4 |
| 5 | 2.5 | 0 | 193.9 ± 3.4 | 96.7 ± 2.6 | 32.4 ± 1.3 |
| 6 | 2.5 | 10 | 214.4 ± 3.9 | 113.3 ± 2.9 | 38.9 ± 0.4 |

It is known from Table 8 that 1α,25-$(OH)_2$-$D_3$ has the function of bone formation; however, when administered solely, its bone dissolving function gains strength as its dosage increases. On the other hand, when 1α,25-$(OH)_2$-$D_3$ is dosed in combination with acetylsalicylic acid, the function of bone formation is performed dominantly.

EXAMPLE 4

1 mg of 1α-OH-$D_3$ was dissolved in 10 g of coconut oil. This solution formed a core substance to provide according to the phase separation technique about 14 g of microcapsules having a diameter of 10 to 50 µm together with a sac substance prepared from 30 g of 10% gelatin aqueous solution and 30 g of 10% acacia aqueous solution.

Capsules, each of which consisted of microcapsules equivalent to 0.5 µg of 1α-OH-$D_3$ and granules which contained 250 mg of acetylsalicylic acid, were prepared according to the ordinary technique.

Another capsules were also prepared with 1α,24-$(OH)_2$-$D_3$ according to the same technique.

EXAMPLE 5

1 ml of an acetone solution containing 1 mg of 1α,24-$(OH)_2D_3$ was added to an aqueous solution containing 10 g of β-cyclic dextrin. The mixture was lyophilized to obtain an inclusion compound of β-cyclic dextrin containing 1α,24-$(OH)_2$-$D_3$.

Pressed tablets were prepared, each consting of the inclusion compound containing 1 µg of 1α,24-$(OH)_2$-$D_3$ and 500 mg of acetylsalicylic acid, according to the ordinary technique.

Another pressed tablets were also obtained with 1α-OH-$D_3$, 1α,25-$(OH)_2$-$D_3$, and 24,25-dihydroxycholecalciferol respectively according to the same method of preparation.

Industrial Application

The bone formation stimulant according to the present invention can be given to human beings to cure or prevent diseases resulting from the vitamin D deficiency or related complications and diseases. As for the diseases for which the bone formation stimulant of the present invention may be usefully administered, the following may be cited: rickets due to deficiency of vitamin D; renal bone dystrophy; parathyroid dysfunction; osteoporosis; betzettis disease; syndrome of absorption disturbance; hypocalcemia due to hepatic induration; hypocalcemia due to steatorrhea; hypocalcemia due to vitamin D resistant rickets; calcium or phosphorus metabolism disturbance resulting from hepatic insufficiency, renal insufficiency, gastrointestinal tract insufficiency or parathyroid insufficiency and related bone diseases.

The bone formation stimulant of the present invention can be used as remedy or preventive for diseases caused by vitamin D deficiency or related diseases including prevention of hypocalcemia of the cow at or near the time of her delivery, prevention of hypocalcemia of domestic animals having no history of hypocalcemia, and prevention of laying soft-shelled eggs among domestic fowls by dosing them during their breeding time.

What is claimed is:

1. A composition for preventing bone salt dissoltuion caused by vitamin $D_3$ or its active derivatives which contains effective amounts of (1) vitamin $D_3$ or an active derivative thereof and (2) acetylsalicylic acid or a pharmaceutically acceptable salt thereof.

2. A composition according to claim 1, wherein the derivative of vitamin $D_3$ is one or more vitamin $D_3$ derivatives selected from the group consisting of 1α-hydroxycholecalciferol, 1α,24(R)-dihydroxycholecalciferol, 1α,25-dihydroxycholecalciferol, and 24,25-dihydroxycholecalciferol.

3. A composition according to claim 1, containing 0.01 to $100 \times 10^{-6}$ part by weight of vitamin $D_3$ or said derivative per 1 part by weight of acetylsalicylic acid or said pharmaceutically acceptable salt.

4. A composition according to claim 1, wherein vitamin $D_3$ or said derivative thereof is stabilized by a β-cyclic dextrin to form an inclusion compound.

* * * * *